US011534713B2

(12) United States Patent
Ward et al.

(10) Patent No.: US 11,534,713 B2
(45) Date of Patent: Dec. 27, 2022

(54) PRODUCT MANIFOLDS FOR USE WITH PORTABLE OXYGEN CONCENTRATORS AND PORTABLE OXYGEN CONCENTRATORS INCLUDING SUCH PRODUCT MANIFOLDS

(71) Applicant: Aventics Corporation, Lexington, KY (US)

(72) Inventors: James R. Ward, Lexington, KY (US); Peizhen Li, Lexington, KY (US)

(73) Assignee: Aventics Corporation, Lexington, KY (US)

( * ) Notice: Subject to any disclaimer, the term of this patent is extended or adjusted under 35 U.S.C. 154(b) by 389 days.

(21) Appl. No.: 16/890,638

(22) Filed: Jun. 2, 2020

(65) Prior Publication Data
US 2020/0384406 A1 Dec. 10, 2020

Related U.S. Application Data

(60) Provisional application No. 62/857,659, filed on Jun. 5, 2019.

(51) Int. Cl.
*B01D 53/047* (2006.01)
*B01D 53/04* (2006.01)
(Continued)

(52) U.S. Cl.
CPC ......... *B01D 53/04* (2013.01); *A61M 16/0063* (2014.02); *A61M 16/101* (2014.02);
(Continued)

(58) Field of Classification Search
CPC ............ A61M 16/0063; A61M 16/101; A61M 16/202; F16K 27/0263; B01D 53/04;
(Continued)

(56) References Cited

U.S. PATENT DOCUMENTS

| 4,385,639 A | 5/1983 | Holborow |
| 5,474,595 A * | 12/1995 | McCombs ........... B01D 53/047 |
| | | 96/144 |

(Continued)

FOREIGN PATENT DOCUMENTS

DE   10-2013-108 418 A1   2/2015

OTHER PUBLICATIONS

International Search Report and Written Opinion for PCT/US2020/035554, dated Oct. 29, 2020.

*Primary Examiner* — Frank M Lawrence, Jr.
(74) *Attorney, Agent, or Firm* — Marshall, Gerstein & Borun LLP (57) ABSTRACT

Product manifolds for use with portable oxygen concentrators and portable oxygen concentrators including such product manifolds. A product manifold for use with a portable oxygen concentrator includes a first product port, a second product port, an accumulator port, an output port, and a flow path. The flow path operatively coupling each of the first product port, the second product port, the accumulator port, and the output port to one another. The product manifold includes a plurality of control ports. Each of the control ports fluidly coupling the flow path. The product manifold includes a first orifice disposed in a first portion of the flow path; a second orifice disposed in a second portion of the flow path; and a third orifice disposed in a third portion of the flow path. Each of the first orifice, the second orifice, and the third orifice being formed by an electrical forming process and having a thickness of between about 0.0025 inches and about 0.004 inches.

20 Claims, 6 Drawing Sheets

(51) Int. Cl.
*A61M 16/00* (2006.01)
*A61M 16/10* (2006.01)
*A61M 16/20* (2006.01)
*F16K 27/02* (2006.01)

(52) U.S. Cl.
CPC ....... *A61M 16/202* (2014.02); *F16K 27/0263* (2013.01); *B01D 2256/12* (2013.01); *B01D 2257/102* (2013.01); *B01D 2259/402* (2013.01); *B01D 2259/40086* (2013.01); *B01D 2259/4533* (2013.01); *B01D 2259/4541* (2013.01)

(58) Field of Classification Search
CPC .......................... B01D 53/0446; B01D 53/053; B01D 53/047; B01D 2256/12; B01D 2257/102; B01D 2257/2259; B01D 2257/40086; B01D 2257/402; B01D 2257/4533; B01D 2257/4541

USPC ................................ 96/121, 152; 95/96, 130
See application file for complete search history.

(56) References Cited

U.S. PATENT DOCUMENTS

| | | | |
|---|---|---|---|
| 7,980,269 | B2 | 7/2011 | Fry et al. |
| 10,188,821 | B2* | 1/2019 | Hojo .................... A61M 16/101 |
| 2006/0230931 | A1* | 10/2006 | Bliss .................... C01B 13/0259 |
| | | | 95/130 |
| 2006/0230939 | A1 | 10/2006 | Bliss et al. |
| 2012/0192864 | A1* | 8/2012 | Galbraith ............... B01D 53/26 |
| | | | 96/111 |
| 2014/0224126 | A1* | 8/2014 | Whitcher ........... B01D 53/0407 |
| | | | 96/121 |
| 2015/0231550 | A1 | 8/2015 | Morita |
| 2015/0260308 | A1 | 9/2015 | Fry et al. |

\* cited by examiner

PRODUCT MANIFOLDS FOR USE WITH PORTABLE OXYGEN CONCENTRATORS AND PORTABLE OXYGEN CONCENTRATORS INCLUDING SUCH PRODUCT MANIFOLDS

FIELD OF THE DISCLOSURE

The present disclosure relates generally to product manifolds and, in particular, to product manifolds for use with portable oxygen concentrators and portable oxygen concentrators including such product manifolds.

BACKGROUND

Portable oxygen concentrators may be used as an alternative to portable oxygen tanks. In operation, portable oxygen concentrators compress and purify ambient air allowing for oxygen-rich air to be delivered to a user.

SUMMARY

In accordance with a first example, a product manifold for use with a portable oxygen concentrator includes a first product port, a second product port, an accumulator port, an output port, and a flow path. The flow path operatively couples each of the first product port, the second product port, the accumulator port, and the output port to one another. The product manifold includes a plurality of control ports. Each of the control ports fluidly couples the flow path. The product manifold includes a first orifice disposed in a first portion of the flow path, a second orifice disposed in a second portion of the flow path, and a third orifice disposed in a third portion of the flow path. Each of the first orifice, the second orifice, and the third orifice are formed by an electrical forming process and have a thickness of between about 0.0025 inches and about 0.004 inches.

In accordance with a second example, a portable oxygen concentrator includes a compressor and a feed/waste manifold. The feed/waste manifold includes an inlet port coupled to the compressor and a pair of three-way valves. Each three-way valve having a first port, a second port, and a third port. The first port being coupled to the compressor. The feed/waste manifold includes an exhaust port. The second port of each of the three-way valves is fluidly coupled to the exhaust port. The portable oxygen concentrator includes a first sieve bed and a second sieve bed. Each of the sieve beds is coupled to the third port of one of the three-way valves. The portable oxygen concentrator includes a product manifold. The product manifold includes a first product port and a second product port. The first product port is coupled to the first sieve bed and the second product port is coupled to the second sieve bed. The product manifold includes an accumulator port, an output port, and a flow path. The flow path fluidly couples the first product port, the second product port, the accumulator port, and the output port to one another. The product manifold also includes a first control port, a second control port, and a third control port. The first, second, and third control ports fluidly couple the flow path. The portable oxygen concentrator includes a first solenoid valve assembly, a second solenoid valve assembly, and a third solenoid valve assembly. Each of the first, second, and third solenoid valve assemblies are secured adjacent to a corresponding one of the first, second, or third control ports. The product manifold includes a first orifice, a second orifice, and a third orifice. The first orifice, the second orifice, and the third orifice are disposed in a corresponding first portion, second portion, or third portion of the flow path. Each of the first orifice, the second orifice, and the third orifice are formed by an electrical forming process.

In accordance with a third example, an orifice for use with a product manifold of a portable oxygen concentrator includes a body. The body has a thickness of between about 0.0025 inches and about 0.004 inches and is formed by an electrical forming process. The body includes a first surface and a second surface opposite the first surface. The body includes a flow hole extending between the first surface and the second surface. The body includes a first edge defined between the flow hole and the first surface. The body includes a second edge defined between the flow hole and the second surface. The first edge is substantially the same as the second edge. The flow hole is adapted to provide a bidirectional flow tolerance of approximately +/−2.5%.

In accordance with a fourth example, a method of producing a product manifold for use with a portable oxygen concentrator includes a first product port, a second product port, an accumulator port, an output port, and a flow path. The flow path fluidly couples the first product port, the second product port, the accumulator port, and the output port to one another. The method includes providing a first product body portion that includes a first orifice bore, a second orifice bore, and a third orifice bore. Each orifice bore is formed by a side wall of the first product body portion and defines a portion of the flow path. The method includes disposing a first orifice, a second orifice, and a third orifice in a corresponding one of the first orifice bore, the second orifice bore, or the third orifice bore. The method includes disposing a first annular seal, a second annular seal, and a third annular seal in a corresponding one of the first, second, or third orifice bores to sealingly engage a corresponding one of the first, second, or third orifices and the side wall of the corresponding orifice bores. The method includes coupling a second product body portion to the first product body portion.

In further accordance with the foregoing first, second, third, and/or fourth examples, an apparatus and/or method may further include any one or more of the following:

In accordance with one example, each of the first orifice, the second orifice, and the third orifice are adapted to provide a bidirectional flow tolerance of approximately +/−2.5%.

In accordance with another example, the first orifice is an oxygen conserving device (OCD) orifice, the second orifice is a purge orifice, and the third orifice is an equalization orifice.

In accordance with another example, further including a plurality of solenoid valve assemblies. The product manifold includes a body and each of the solenoid valve assemblies is secured to the body of the product manifold adjacent to a corresponding one of the control ports.

In accordance with another example, the first portion of the flow path includes a first orifice bore, the second portion of the flow path includes a second orifice bore, and the third portion of the flow path includes a third orifice bore.

In accordance with another example, further including a gasket track and a gasket. The gasket track is coupled to the first orifice bore, the second orifice bore, and the third orifice bore. The gasket is disposed within the gasket track and the first orifice bore, the second orifice bore, and the third orifice bore.

In accordance with another example, the gasket track includes opposing walls. The first orifice bore is coupled to the gasket track via a first opening, the second orifice bore is coupled to the gasket track via a second opening and a third opening, and the third orifice bore is coupled to the gasket track via a fourth opening, a fifth opening, and a sixth opening. The gasket is adapted to sealingly engage the opposing walls of the gasket track adjacent the first, second, third, fourth, fifth, and sixth openings.

In accordance with another example, the gasket includes a first radial extension. The first radial extension extends through the first opening and sealingly engages the opposing walls adjacent the first opening.

In accordance with another example, the product manifold includes a first product body portion and a second product body portion. The gasket is disposed between the first product body portion and the second product body portion. The first radial extension includes a recess. The recess is adapted to allow the gasket to fill the gasket track when the first product body portion is coupled to the second product body portion.

In accordance with another example, the first portion includes a first orifice bore having a first side wall. Further including an annular seal that is disposed within the first orifice bore and sealingly engages the first orifice and the first side wall.

In accordance with another example, the first portion includes a first orifice bore having a first side wall. A gap is defined between a perimeter of the first orifice and the first side wall.

In accordance with another example, the first orifice has a thickness of between about 0.0025 inches and about 0.004 inches.

In accordance with another example, the first orifice is adapted to provide a bidirectional flow tolerance of approximately +/−2.5%.

In accordance with another example, the first orifice has a first flow hole, a first surface, and a second surface opposite the first surface. A first edge is defined between the first flow hole and the first surface and a second edge is defined between the first flow hole and the second surface. The first edge is substantially the same as the second edge.

In accordance with another example, the first portion of the flow path includes a first orifice bore having a first side wall, the second portion of the flow path includes a second orifice bore having a second side wall, and the third portion of the flow path includes a third orifice bore having a third side wall. Further including a first annular seal, a second annular seal, and a third annular seal. The first, second, and third annular seals are disposed in a corresponding one of the first, second, or third orifice bores and sealingly engage a corresponding one of the first, second, or third orifices and a corresponding one of the first, second, or third side walls of the orifice bores.

In accordance with another example, further including a gasket that includes the first annular seal, the second annular seal, and the third annular seal. The first product manifold includes a gasket track that is coupled to the first orifice bore, the second orifice bore, and the third orifice bore. The gasket is disposed within the gasket track.

In accordance with another example, the first orifice, the second orifice, and the third orifice are formed by an electrical forming process.

In accordance with another example, the first orifice has a thickness of between about 0.0025 inches and about 0.004 inches.

DETAILED DESCRIPTION

Although the following text discloses a detailed description of example methods, apparatus, and/or articles of manufacture, it should be understood that the legal scope of the property right is defined by the words of the claims set forth at the end of this patent. Accordingly, the following detailed description is to be construed as examples only and does not describe every possible example, as describing every possible example would be impractical, if not impossible. Numerous alternative examples could be implemented, using either current technology or technology developed after the filing date of this patent. It is envisioned that such alternative examples would still fall within the scope of the claims.

Figure 1:
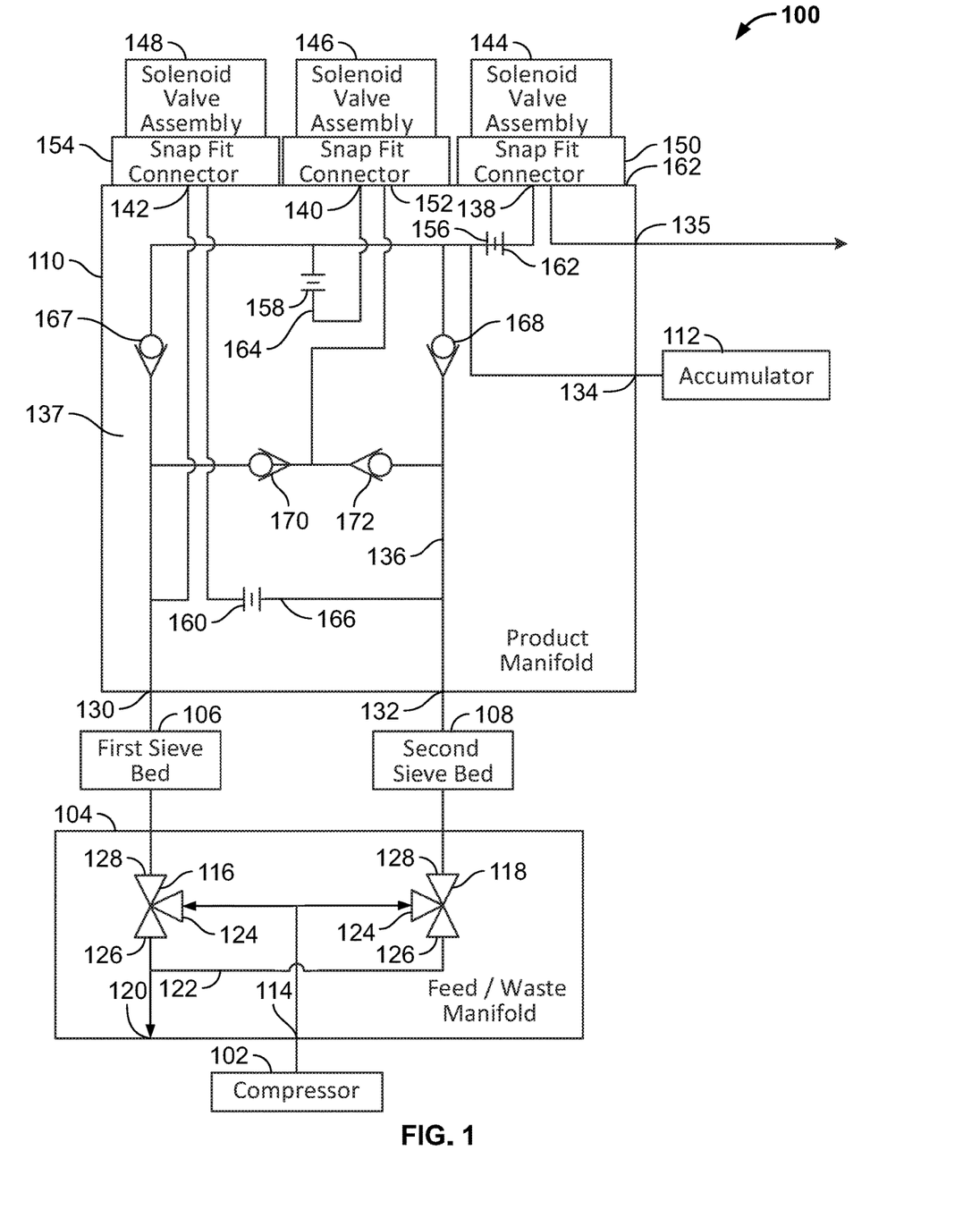
FIG. 1 illustrates a portable oxygen concentrator assembled in accordance with a first disclosed example of the present invention.

Referring now to the drawings, FIG. 1 illustrates a portable oxygen concentrator 100 assembled in accordance with a first disclosed example of the present invention. In accordance with the disclosed example, the portable oxygen concentrator 100 includes a compressor 102, a feed/waste manifold 104, first and second sieve beds 106, 108, a product manifold 110, and an accumulator 112.

The compressor 102 is adapted to draw in ambient air, compress that air, and provide the compressed air to the feed/waste manifold 104.

The feed/waste manifold 104 is adapted to receive the compressed air from the compressor 102 and provide the compressed ambient air to the sieve beds 106, 108. The feed/waste manifold 104 is also adapted to receive nitrogen rich air from the sieve beds 106, 108 during a purge operation.

In the example shown, the feed/waste manifold 104 includes an inlet port 114, a pair of three-way valves 116, 118, an exhaust port 120, and a flow path 122. The inlet port 114 of the feed/waste manifold 104 is coupled to the compressor 102. Each of the valves 116, 118 includes a first port 124, a second port 126, and a third port 128. The first port 124 of each of the valves 116, 118 of the feed/waste manifold 104 is coupled to the compressor 102 via the inlet port 114 and the flow path 122. The second port 126 of each of the valves 116, 118 of the feed/waste manifold 104 is coupled to the exhaust port 120 via the flow path 122.

The first sieve bed 106 and the second sieve bed 108 are each coupled to the third port 128 of one the valves 116, 118.

The sieve beds 106, 108 are adapted to adsorb nitrogen from the pressurized ambient air received from the feed/waste manifold 104, for example.

The product manifold 110 is adapted to receive oxygen-rich air from the sieve beds 106, 108 and to provide the oxygen-rich air to the accumulator 112 or to a patient. The product manifold 110 is also adapted to perform a purging operation where a portion of the oxygen-rich air is back flushed through the sieve beds 106, 108 to remove accumulated nitrogen within the sieve beds 106, 108. The nitrogen removed from the sieve beds 106, 108 can thereafter be exhausted via the exhaust port 120 of the feed/waste manifold 104.

In the example shown, the product manifold 110 includes a first product port 130, a second product port 132, an accumulator port 134, an outlet port 135, and a flow path 136. The first product port 130 is coupled to the first sieve bed 106 and the second product port 132 is coupled to the second sieve bed 108. The flow path 136 fluidly couples the first product port 130, the second product port 132, the accumulator port 134, and the output port 135.

The product manifold 110 also includes a body 137, a first control port 138, a second control port 140, and a third control port 142. The first, second, and third control ports 138, 140, 142 fluidly couple portions of the flow path 136. In the example shown, the first control port 138 is an oxygen conserving device (OCD) port, the second control port 140 is a purge port, and the third control port 142 is an equalization port. However, the arrangement of the control ports 138, 140, 142 may be changed. Further, a different number of control ports (e.g., 1 control p ort, 2 control ports, 4 control ports) may be provided.

The product manifold 110 includes a first solenoid valve assembly 144, a second solenoid valve assembly 146, and a third solenoid valve assembly 148. Each of the first, second, and third solenoid valve assemblies 144, 146, 148 is secured to the body 137 of the product manifold 110 by a snap fit connector 150, 152, 154. Alternatively, one or more of the solenoid valve assemblies 144, 146, 148 may be secured to the body 137 of the product manifold 110 in a different way. For example, a threaded coupling may be provided between the solenoid valve assembly 144, 146, 148 and the body 137 of the product manifold 110.

In the example shown, each solenoid valve assembly 144, 146, 148 is secured to the body 137 of the product manifold 110 adjacent to a corresponding one of the first, second, or third control ports 138, 140, 142. Thus, the solenoid valve assemblies 144, 146, 148 are adapted to control fluid flow through the respective control ports 138, 140, 142.

Figure 8:
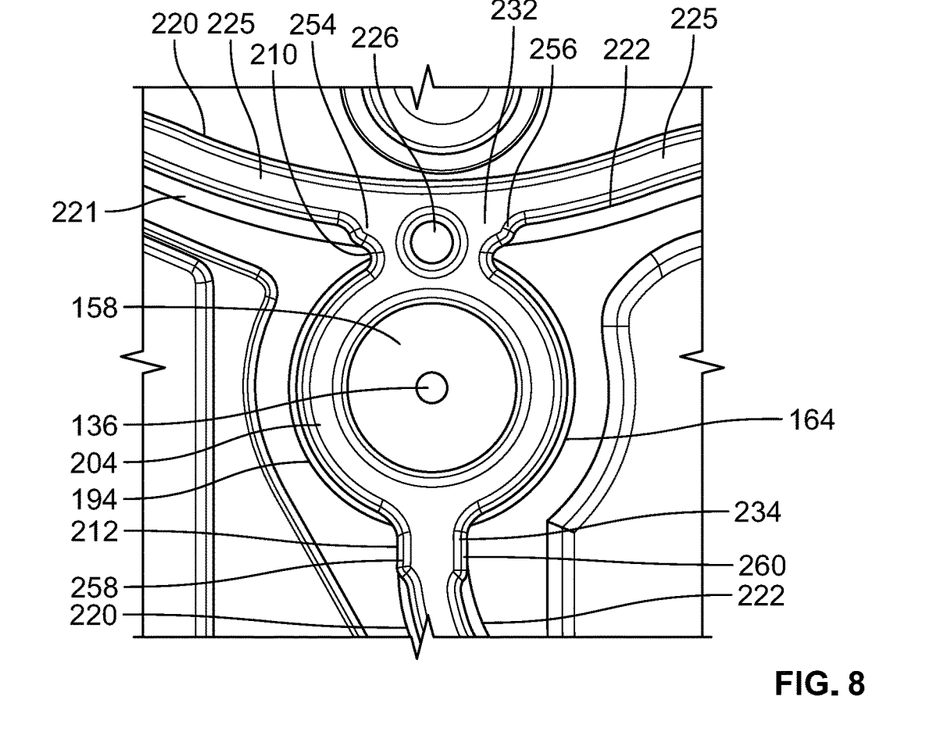
FIG. 8 illustrates a fragmented top view of the second orifice bore, the second orifice, and the second annular seal of the product manifold of FIG. 4.
Figure 9:
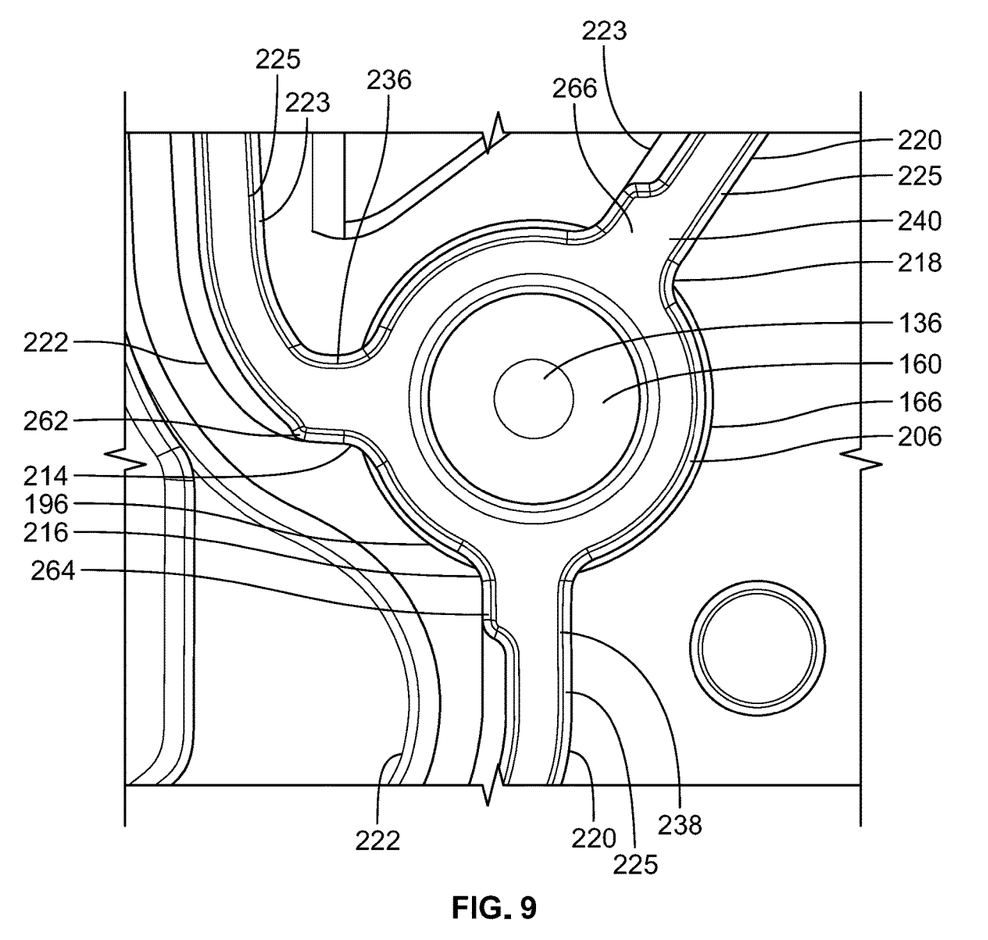
FIG. 9 illustrates a fragmented top view of the third orifice bore, the third orifice, and the third annular seal of the product manifold of FIG. 4.

The product manifold 110 also includes a first orifice 156 (the first orifice 156 is most clearly shown in FIG. 2), a second orifice 158 (the second orifice 158 is most clearly shown in FIG. 8), and a third orifice 160 (the third orifice 160 is most clearly shown in FIG. 9). The first orifice 156 may be referred to as an oxygen conserving device (OCD) orifice, the second orifice 158 may be referred to as a purge orifice, and the third orifice 160 may be referred to as an equalization orifice.

The first and third orifices 156, 160 may be similarly sized and the second orifice 158 may be a different size from the first and third orifices 156, 160. The first orifice 156 is disposed within a first portion 162 of the flow path 136, the second orifice 158 is disposed within a second portion 164 of the flow path 136, and the third orifice 160 is disposed within a third portion 166 of the flow path 136. In the disclosed example, each of the first orifice 156, the second orifice 158, and the third orifice 160 are formed by an electrical forming process. In an example, the orifices 156, 158, 160 are adapted to provide a bidirectional flow tolerance of approximately +/−2% or +/−2.5% and have a thickness of between about 0.0025 inches and about 0.004 inches. However, the orifices 156, 158, 160 may have a different thickness. Further, while the orifices 156, 158, 160 are disclosed as being formed using an electrical forming process, the orifices 156, 158, and/or 160 may be formed using other methods. For example, laser cutting methods, water jetting methods, electrical discharge machining (EDM) methods, etc. may be used.

The product manifold 110 also includes a first check valve 167 and a second check valve 168. The first check valve 167 is associated with receiving air from the first sieve bed 106 and the second check valve 168 is associated with receiving air from the second sieve bed 108. The check valves 167, 168 are adapted to allow the flow of oxygen-rich air from the sieve beds 106, 108 toward the accumulator 112 or toward the first control port 138. Specifically, to allow the oxygen-rich air received from the sieve beds 106 and/or 108 to flow out of the outlet port 135 of the product manifold 110, the first solenoid valve assembly 144 moves to the open position to allow the oxygen-rich air to flow through the OCD orifice 156, the first control port 138, and out of the outlet port 135 toward, for example, a patient.

The product manifold 110 also includes a third check valve 170 and a fourth check valve 172. The third check valve 170 is associated with flowing air toward the first sieve bed 106 during a purge operation and the fourth check valve 172 is associated with flowing air toward the second sieve bed 108 during a purge operation. Specifically, during a purge operation, the second solenoid valve assembly 146 moves to an open position and allows the oxygen-rich air to back flow through the purge orifice 158, through the second control port 140, through the third and fourth check valves 170, 172, and toward the sieve beds 106, 108.

In the example shown, to perform an equalization operation between the first and second sieve beds 106, 108, the third solenoid valve assembly 148 moves to the open position to allow air to flow between the first sieve bed 106 and the second sieve bed 108 and through the equalization orifice 160.

Figure 2:
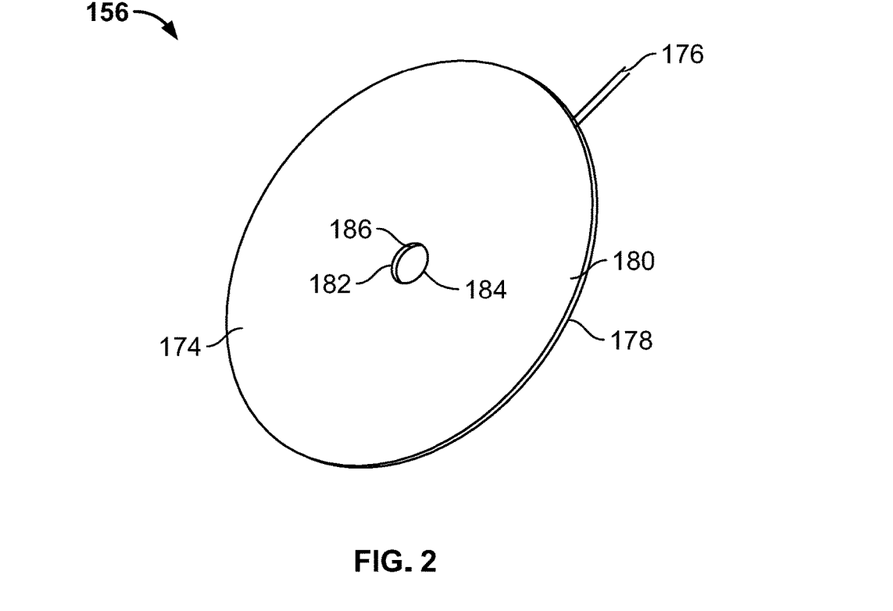
FIG. 2 illustrates an isometric view of a specific example of the first orifice of a product manifold of the portable oxygen concentrator of FIG. 1.
Figure 3:
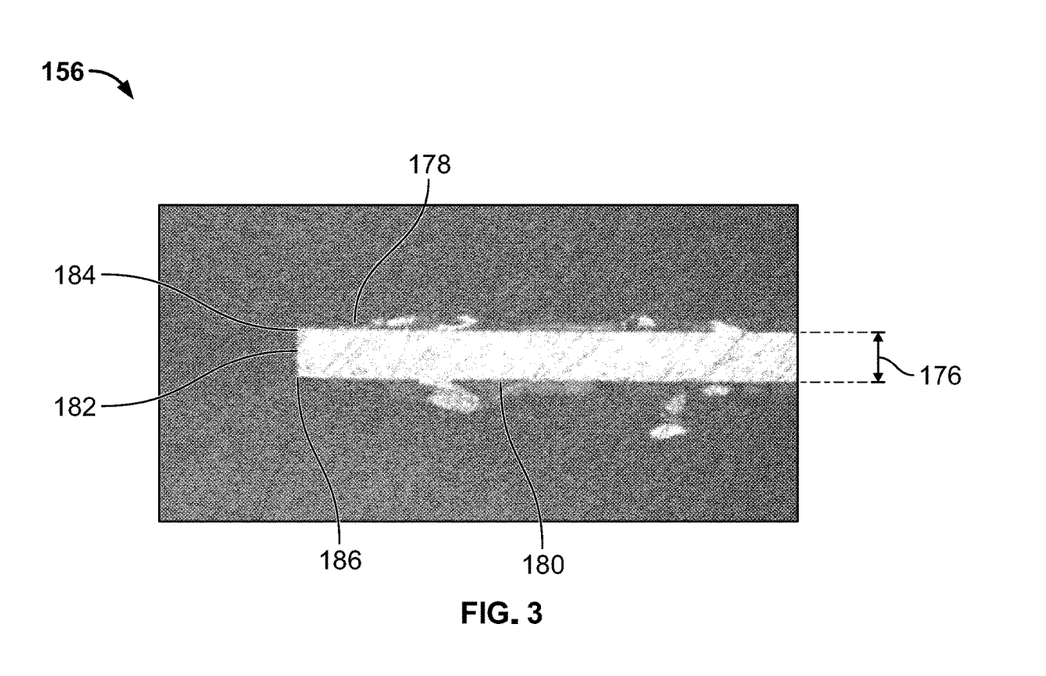
FIG. 3 illustrates an expanded fragmented view of the first orifice of FIG. 2.

FIG. 2 illustrates an isometric view of a specific example of the OCD orifice 156 of the product manifold 110 of FIG. 1. FIG. 3 illustrates an expanded fragmented view of the OCD orifice 156 of FIG. 2.

In the example shown, the first orifice 125 includes a body 174. The body 174 has a thickness 176 of between about 0.0025 inches and about 0.004 inches and is formed by an electrical forming process. The body 174 has a first surface 178 and a second surface 180 opposite the first surface 178. A flow hole 182 extends between the first surface 178 and the second surface 180. A first edge 184 is defined between the flow hole 182 and the first surface 178 and a second edge 186 is defined between the flow hole 182 and the second surface 180. In the example shown, the first edge 184 is substantially the same as the second edge 186. As set forth herein, the phrase "substantially the same" accounts for manufacturing between the first edge 184 and the second edge 186. Thus, the first edge 184 and the second edge 186 are symmetric. Further, in the example shown, the flow hole 182 is adapted to provide a bidirectional flow tolerance of approximately +/−2.5% or approximately +/−2.0%. However, other flow tolerances may be achieved using the disclosed orifices such as, for example. +/−2.1%, +/−2.2%, +/−2.35%, etc.

Referring to FIG. 3, the first and second edges 184, 186 each form approximately a 90° corner. However, in an alternative example when the first orifice 125 is formed having a thickness of, for example, approximately 0.10 inches, the first edge 184 may not be substantially the same as the second edge 186. For example, the first edge 184 may be rounded and the second edge 186 may form a sharp corner (e.g., approximately a 90° angle). If the first and second edges 184, 186 are different from one another, air flowing in different directions through the flow hole 182 may have different flow characteristics. Thus, a bidirectional flow tolerance of approximately +/−2.5% may not be achievable. While the OCD orifice 156 is shown in FIGS. 2 and 3, the second and third orifices 158, 160 may be similar or the same.

Figure 4:
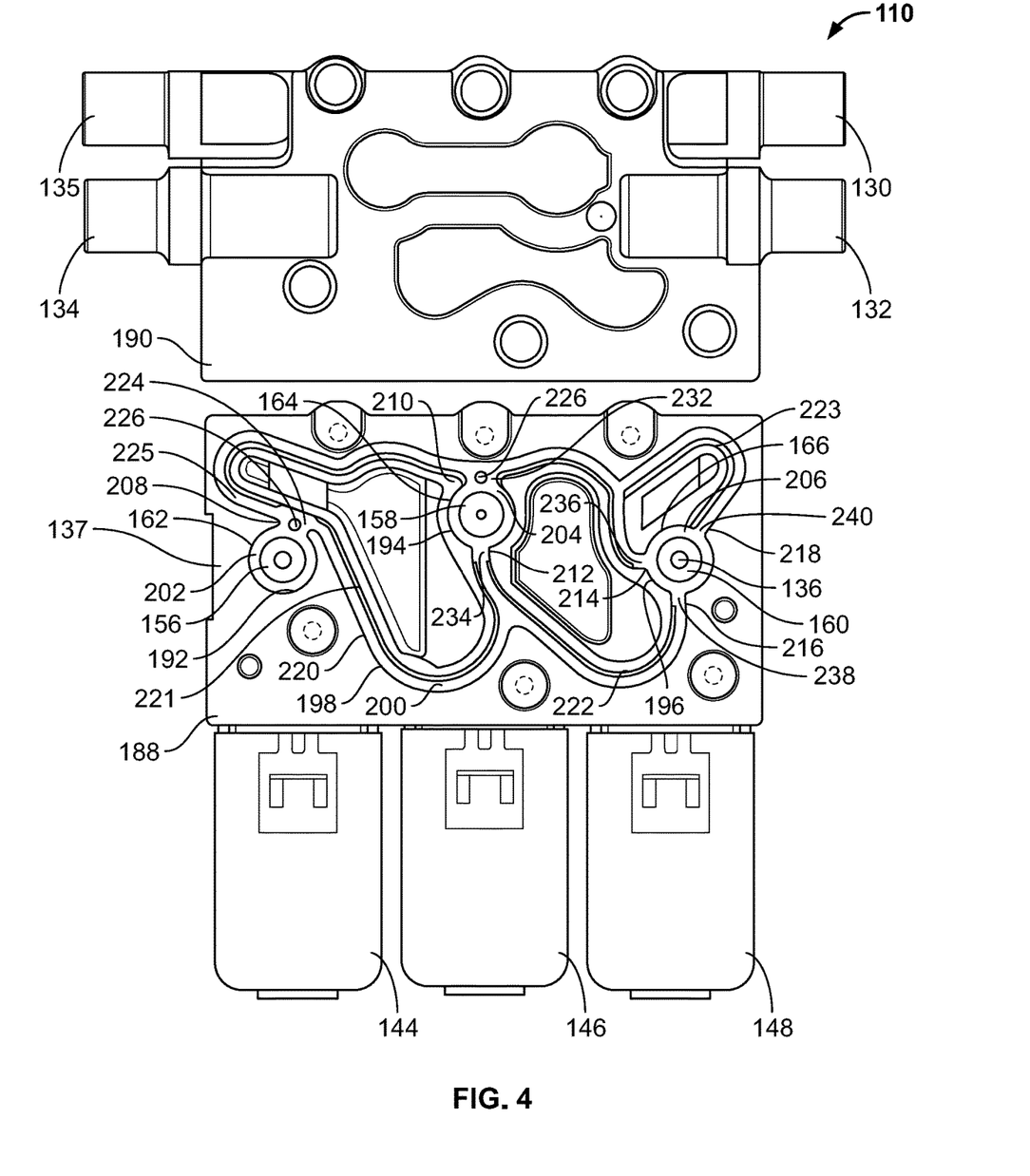
FIG. 4 illustrates a partially expanded top view of a specific implementation of the product manifold of FIG. 1.
Figure 5:
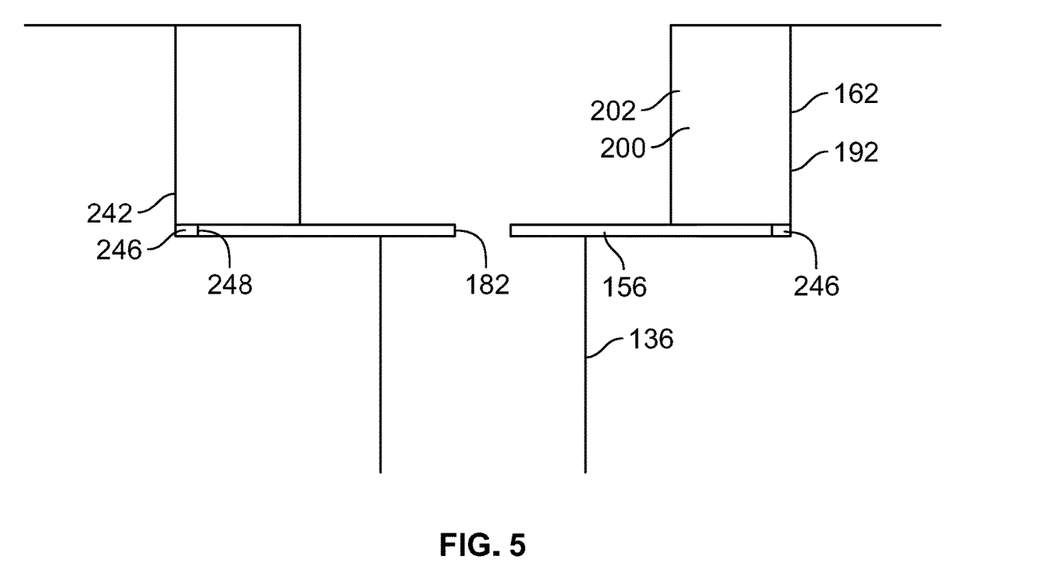
FIG. 5 illustrates a schematic enlarged fragmented view of the first orifice and the first portion of the flow path of the product manifold of FIG. 4.
Figure 6:
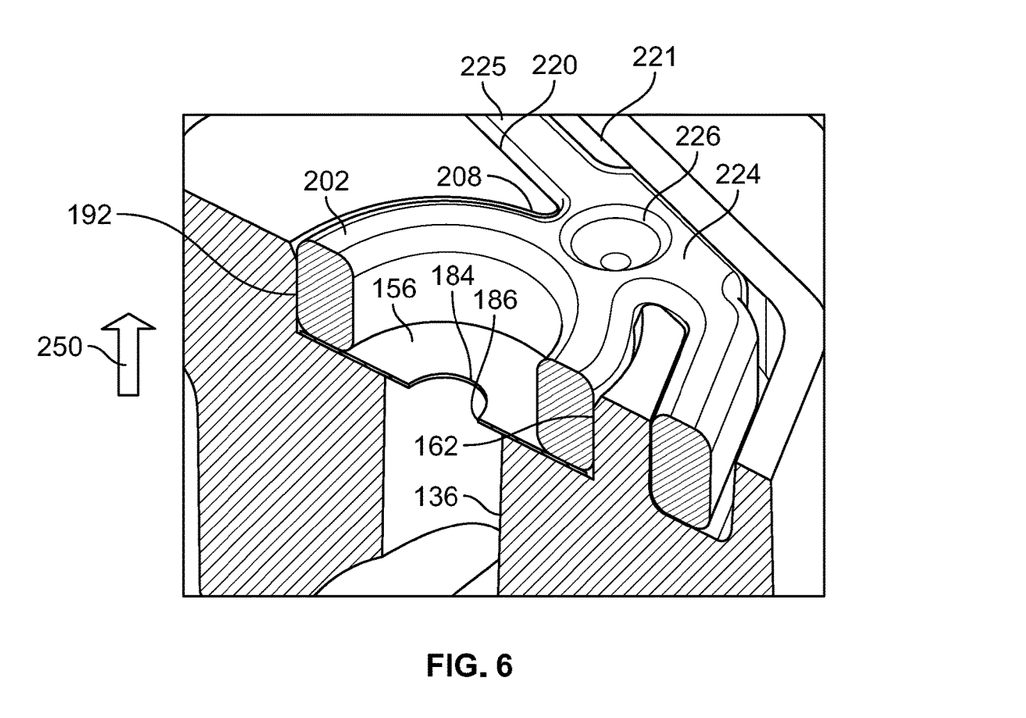
FIG. 6 illustrates an enlarged fragmented isometric view of the first orifice and the first portion of the flow path of the product manifold of FIG. 4.
Figure 7:
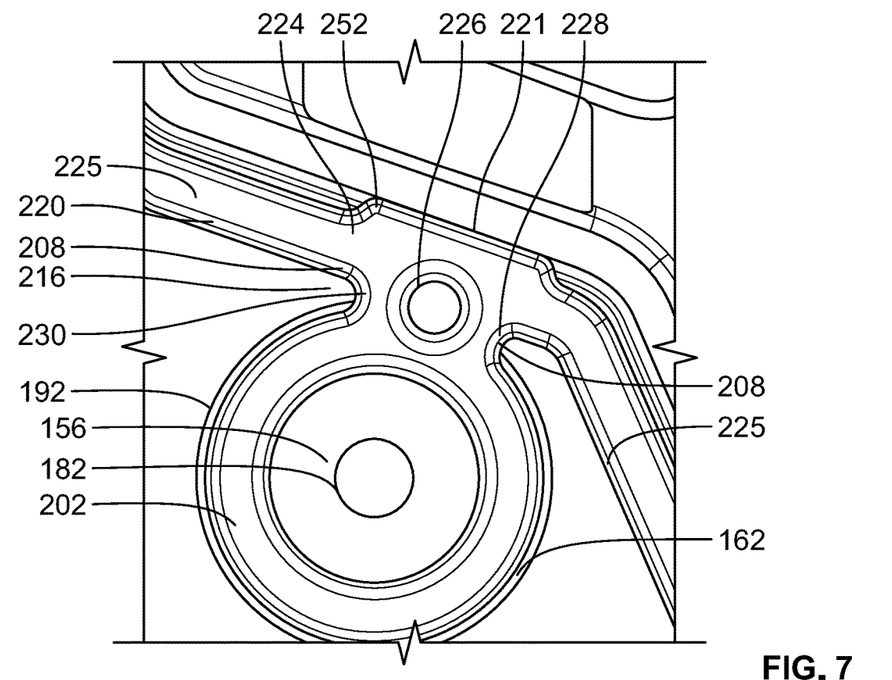
FIG. 7 illustrates an enlarged fragmented top view of the first orifice bore, the first orifice and the first portion of the flow path of the product manifold of FIG. 4.

FIG. 4 illustrates a partially expanded top view of a specific implementation of the product manifold 110 of FIG. 1; FIG. 5 illustrates a schematic enlarged fragmented view of the OCD orifice 156 and the first portion 162 of the flow path 136 of FIG. 4; FIG. 6 illustrates an enlarged fragmented isometric view the OCD orifice 156 and the first portion 162 of the flow path 136 of FIG. 4; and FIG. 7 illustrates an enlarged fragmented top view of the OCD orifice 156 and the first portion 162 of the flow path 136 of FIG. 4.

Referring to FIG. 4, with reference to FIGS. 5, 6, 7, 8, and 9, the product manifold 110 includes a first product body portion 188 and a second product body portion 190. In the example shown, the first portion 162 of the flow path 136 is formed as a first orifice bore 192 (the first orifice bore 192 is most clearly shown in FIGS. 5 and 6), the second portion 164 of the flow path 136 is formed as a second orifice bore 194 (the second orifice bore 194 is mostly clearly shown in FIG. 8), and the third portion 166 of the flow path 136 is formed as a third orifice bore 196 (the third orifice bore 196 is most clearly shown in FIG. 9).

The body 137 of the product manifold 110 and, specifically, the first body portion 188 of the product manifold 110, defines a gasket track 198. The gasket track 198 is coupled to each of the first orifice bore 192, the second orifice bore 194, and the third orifice bore 196. A gasket 200 is disposed within the gasket track 198 and the first bore orifice 192, the second orifice bore 194, and the third orifice bore 196. The gasket 200 is also disposed between the first and second product body portions 188, 190 when the first and second product body portions 188, 190 are coupled together.

In the example shown, the gasket 200 includes a first annular seal 202, a second annular seal 204, and a third annular seal 206. The first, second, and third annular seals 202, 204, 206 are disposed within the corresponding first, second, or third orifice bores 192, 194, or 196. The first orifice bore 192 is coupled to the gasket track 198 via a first opening 208, the second orifice bore 194 is coupled to the gasket track 198 via a second opening 210 and a third opening 212, and the third orifice bore 196 is coupled to the gasket track 198 via a fourth opening 214, a fifth opening 216, and a sixth opening 218.

The gasket track 198 includes opposing walls 220, 221, 222, 223 and the gasket 200 is adapted to sealingly engage the corresponding opposing walls 220, 221, 222, 223 adjacent the first, second, third, fourth, fifth, and sixth openings 208 through 218. In the example shown, the gasket 200 includes a first radial extension 224 (the first radial extension 224 is most clearly shown in FIG. 7). The first radial extension 224 is coupled to the first annular seal 202, extends through the first opening 208, and sealingly engages the opposing walls 220, 221 adjacent the first opening 208. The first radial extension 244 is wider than a portion 225 of the gasket 200 that extends from the first radial extension 244. Thus, in the example shown, the portion 225 of the gasket 200 engages the wall 220 of the gasket track 198 and is spaced from the opposing wall 221 of the gasket track 198. Alternatively, the portion 225 of the gasket 200 may be positioned between the walls 220, 221 or engage the other one of the walls 221 of the gasket track 198.

The first radial extension 224 includes a recess 226. The recess 226 is adapted to allow the gasket 200 to fill the gasket track 198 when the first product body portion 188 is coupled to the second product body portion 190. Notches 228, 230 (the notches 228, 230 are most clearly shown in FIG. 7) are defined between the first radial extension 224 and the first annular seal 202. The notches 228, 230 are adapted to receive the first product body portion 188 adjacent the first opening 208.

The gasket 200 also includes second and third radial extensions 232, 234 that are coupled to the second annular seal 204. The second and third radial extensions 232, 234 extend through the corresponding second and third opening 210, 212 and sealingly engage the opposing walls 220, 221, 222 and 220, 222 adjacent the second and third opening 210, 212. In the example shown, the second radial extension 232 includes the recess 226 but the third radial extension 234 does not include the recess 226. The second and third radial extensions 232, 234 are wider than the portion 225 of the gasket 200 adjacent thereto. As a result of the thickness of the portion 225 of the gasket 200, when the first product body portion 188 is coupled to the second product body portion 190, the gasket 200 may expand into areas of the gasket track 198 not occupied by the gasket 200 when, for example, the gasket 200 is not compressed.

Similarly, the gasket 200 includes fourth, fifth, and sixth radial extensions 236, 238, 240 that are coupled to the third annular seal 206. The fourth, fifth, and sixth radial extensions 236, 238, 240 extend through the corresponding fourth, fifth, and sixth openings 214, 216, 218 and sealingly engage the opposing walls 220, 222 and 220, 223 adjacent the fourth, fifth, and sixth openings 214, 216, 218.

Referring to FIG. 5, the first orifice bore 192 includes a first side wall 242. The first annular seal 202 of the gasket 200 is disposed within the first orifice bore 192 and sealingly engages the OCD orifice 156 and the first side wall 242. As a result, fluid (e.g., air) is substantially prevented from flowing between an interface between the first annular seal 202 and the first side wall 242 and an interface between the first annular seal 202 and the OCD orifice 156. The sealing engagement between the radial extensions 224 and 232 through 240 and the opposing walls 220, 221, 222, 223 of the gasket track 198 substantially prevents fluid from flowing through an interface between the annular seals 202, 204, 206 and the corresponding walls 220, 221, 222, 223.

A gap 246 is provided between a perimeter 248 of the OCD orifice 156 and the first side wall 242. Thus, in the example shown, the OCD orifice 156 is secured within the first orifice bore 192 via the gasket 200. An interference fit between the OCD orifice 156 and the first side wall 242 is not provided because of the gap 246.

FIG. 6 illustrates a fragmented cross-sectional view of the first orifice bore 192, the OCD orifice 156, and the first annular seal 202. In the example shown, the first edge 184 of the OCD orifice 156 faces in a direction generally indicated by arrow 250 and the second edge 186 of the OCD orifice 156 faces in a direction generally opposite that indicated by the arrow 250.

FIG. 7 illustrates a fragmented top view of the first orifice bore 192, the OCD orifice 156, and the first annular seal 202.

The first radial extension 224 includes a protrusion 252. The protrusion may have a cross-section that substantially forms an isosceles trapezoid. In the example shown, the protrusion 252 and another portion of the first radial extension 224 fill the space between the walls 220, 221 of the gasket track 198 adjacent the first opening 208. Thus, the protrusion 252 and the other portion of the first radial extension 224 are positioned between the opposing walls 220, 221 to substantially prevent air from flowing into the first orifice bore 192 via the first opening 208. However, the protrusion 252 may have a different cross-section to substantially ensure sealing engagement between the gasket 200 and the opposing walls 220, 221.

FIG. 8 illustrates a fragmented top view of the second orifice bore 194, the purge orifice 158, and the second annular seal 204. In the example shown, the second radial extension 232 includes protrusions 254, 256. The protrusion 254, 256 extend toward and engage the walls 221, 222 on either side of the second opening 210. The sealing engagement provided by the protrusions 254, 256 and another portion of the second radial extension 232 substantially prevents air from flowing into the second orifice bore 194 via the second opening 210. Additionally, in the example shown, the third radial extension 234 includes lateral extensions 258, 260. The lateral extensions 258, 260 extend toward and engage the walls 220, 222 on either side of the third opening 212.

FIG. 9 illustrates a fragmented top view of the third orifice bore 196, the equalization orifice 160, and the third annular seal 206. In the example shown, each of the fourth, fifth, and sixth radial extensions 236, 238, 240 have a single lateral extension 262, 264, 266. The lateral extensions 262, 264, 266 extend toward and engage corresponding walls 222 and 223 of the gasket track 198 to seal the openings 214, 216, 218 into the third orifice bore 196.

Further, while several examples have been disclosed herein, any features from any examples may be combined with or replaced by other features from other examples. Moreover, while several examples have been disclosed herein, changes may be made to the disclosed examples within departing from the scope of the claims.

What is claimed is:

1. A product manifold for use with a portable oxygen concentrator, the product manifold, comprising:
   a first product port, a second product port, an accumulator port, and an output port;
   a flow path operatively coupling each of the first product port, the second product port, the accumulator port, and the output port to one another;
   a plurality of control ports, each of the control ports fluidly coupling the flow path;
   a first orifice disposed in a first portion of the flow path;
   a second orifice disposed in a second portion of the flow path; and
   a third orifice disposed in a third portion of the flow path;
   each of the first orifice, the second orifice, and the third orifice being formed by an electrical forming process and having a thickness of between about 0.0025 inches and about 0.004 inches.

2. The product manifold of claim 1, wherein each of the first orifice, the second orifice, and the third orifice are adapted to provide a bidirectional flow tolerance of approximately +/−2.5%.

3. The product manifold of claim 1, wherein the first orifice is an oxygen conserving device (OCD) orifice, the second orifice is a purge orifice, and the third orifice is an equalization orifice.

4. The product manifold of claim 1, further comprising a plurality of solenoid valve assemblies, wherein the product manifold comprises a body and wherein each of the solenoid valve assemblies is secured to the body of the product manifold adjacent to a corresponding one of the control ports.

5. The product manifold of claim 1, wherein the first portion of the flow path comprises a first orifice bore, the second portion of the flow path comprises a second orifice bore, and the third portion of the flow path comprises a third orifice bore.

6. The product manifold of claim 5, further comprising a gasket track and a gasket, the gasket track being coupled to the first orifice bore, the second orifice bore, and the third orifice bore, the gasket being disposed within the gasket track and the first orifice bore, the second orifice bore, and the third orifice bore.

7. The product manifold of claim 6, wherein the gasket track comprises opposing walls, and wherein the first orifice bore is coupled to the gasket track via a first opening, the second orifice bore is coupled to the gasket track via a second opening and a third opening, and the third orifice bore is coupled to the gasket track via a fourth opening, a fifth opening, and a sixth opening, the gasket being adapted to sealingly engage the opposing walls of the gasket track adjacent the first, second, third, fourth, fifth, and sixth openings.

8. The product manifold of claim 7, wherein the gasket comprises a first radial extension, wherein the first radial extension extends through the first opening and sealingly engages the opposing walls adjacent the first opening.

9. The product manifold of claim 8, wherein the product manifold comprises a first product body portion and a second product body portion, the gasket being disposed between the first product body portion and the second product body portion, wherein the first radial extension comprises a recess, the recess being adapted to allow the gasket to fill the gasket track when the first product body portion is coupled to the second product body portion.

10. The product manifold of claim 1, wherein the first portion comprises a first orifice bore having a first side wall, further including an annular seal, the annular seal being disposed within the first orifice bore and sealingly engages the first orifice and the first side wall.

11. The product manifold of claim 1, wherein the first portion comprises a first orifice bore having a first side wall, wherein a gap is defined between a perimeter of the first orifice and the first side wall.

12. A portable oxygen concentrator, comprising:
   a compressor;
   a feed/waste manifold, comprising:
   an inlet port coupled to the compressor;
   a pair of three-way valves, each three-way valve having a first port, a second port, and a third port, the first port coupled to the compressor; and
   an exhaust port, the second port of each of the three-way valves being fluidly coupled to the exhaust port;
   a first sieve bed and a second sieve bed, each of the sieve beds being coupled to the third port of one of the three-way valves;
   a product manifold, comprising:
   a first product port and a second product port, the first product port coupled to the first sieve bed, the second product port coupled to the second sieve bed;
   an accumulator port;
   an output port;

a flow path, the flow path fluidly coupling the first product port, the second product port, the accumulator port, and the output port to one another;

a first control port, a second control port, and a third control port fluidly coupling the flow path;

a first solenoid valve assembly, a second solenoid valve assembly, and a third solenoid valve assembly, each of the first, second, and third solenoid valve assemblies being secured adjacent to a corresponding one of the first, second, or third control ports; and a first orifice, a second orifice, and a third orifice, the first orifice, the second orifice, and the third orifice being disposed in a corresponding first portion, second portion, or third portion of the flow path, each of the first orifice, the second orifice, and the third orifice being formed by an electrical forming process.

13. The portable oxygen concentrator of claim 12, wherein the first orifice has a thickness of between about 0.0025 inches and about 0.004 inches.

14. The portable oxygen concentrator of claim 12, wherein the first orifice is adapted to provide a bidirectional flow tolerance of approximately +/−2.5%.

15. The portable oxygen concentrator of claim 12, wherein the first orifice comprises a first flow hole, a first surface, and a second surface opposite the first surface, a first edge being defined between the first flow hole and the first surface and a second edge being defined between the first flow hole and the second surface, the first edge being substantially the same as the second edge.

16. The portable oxygen concentrator of claim 12, wherein the first portion of the flow path comprises a first orifice bore having a first side wall, the second portion of the flow path comprises a second orifice bore having a second side wall, and the third portion of the flow path comprises a third orifice bore having a third side wall, further comprising a first annular seal, a second annular seal, and a third annular seal, the first, second, and third annular seals being disposed in a corresponding one of the first, second, or third orifice bores and sealingly engaging a corresponding one of the first, second, or third orifices and a corresponding one of the first, second, or third side walls of the orifice bores.

17. The portable oxygen concentrator of claim 16, further comprising a gasket, the gasket comprises the first annular seal, the second annular seal, and the third annular seal, wherein the first product manifold comprises a gasket track, the gasket track being coupled to the first orifice bore, the second orifice bore, and the third orifice bore, the gasket being disposed within the gasket track.

18. The portable oxygen concentrator of claim 17, wherein the gasket track comprises opposing walls, the first orifice bore being coupled to the gasket track via a first opening, the second orifice bore being coupled to the gasket track via a second opening, and a third opening, and the third orifice bore being coupled to the gasket track via a fourth opening, a fifth opening, and a sixth opening, the gasket being adapted to sealingly engage the opposing walls of the gasket track adjacent the first, second, third, fourth, fifth, and sixth openings.

19. An orifice for use with a product manifold of a portable oxygen concentrator, the orifice comprising:

a body having a thickness of between about 0.0025 inches and about 0.004 inches and being formed by an electrical forming process, the body comprising:

a first surface and a second surface opposite the first surface;

a flow hole extending between the first surface and the second surface;

a first edge being defined between the flow hole and the first surface; and a second edge being defined between the flow hole and the second surface, the first edge being substantially the same as the second edge, wherein the flow hole is adapted to provide a bidirectional flow tolerance of approximately +/−2.5%.

20. The orifice of claim 19, wherein the orifice is one of an oxygen conserving device (OCD) orifice, a purge orifice, or an equalization orifice.

* * * * *

UNITED STATES PATENT AND TRADEMARK OFFICE
CERTIFICATE OF CORRECTION

PATENT NO. : 11,534,713 B2
APPLICATION NO. : 16/890638
DATED : December 27, 2022
INVENTOR(S) : James R. Ward et al.

It is certified that error appears in the above-identified patent and that said Letters Patent is hereby corrected as shown below:

In the Specification

Column 4, Line 67, "one the" should be -- one of the --.

Column 5, Line 31, "p ort," should be -- port, --.

Column 7, Line 21, "view the" should be -- view of the --.

Column 7, Line 67, "244" should be -- 224 --.

Column 8, Line 2, "244." should be -- 224. --.

Signed and Sealed this
Tenth Day of December, 2024

Katherine Kelly Vidal
*Director of the United States Patent and Trademark Office*